United States Patent [19]

Dietz

[11] Patent Number: 4,745,925
[45] Date of Patent: May 24, 1988

[54] OPTOELECTRONIC INHALATION SENSOR FOR MONITORING INHALATION AND FOR INHALATION THERAPY

[76] Inventor: Henry G. Dietz, 80 Salisbury Ave., Garden City, N.Y. 11530

[21] Appl. No.: 916,660

[22] Filed: Oct. 6, 1986

[51] Int. Cl.[4] ............................................. A61B 5/08
[52] U.S. Cl. ...................................... 128/725; 73/705
[58] Field of Search .............. 128/725, 727, 728, 782, 128/721; 73/861.47, 705

[56] References Cited

U.S. PATENT DOCUMENTS 3,946,726  3/1976  Pikul .................................... 128/725
4,360,247  11/1982  Beasley ................................ 73/705
4,526,041  7/1985  Beller et al. ...................... 73/861.47
4,546,793  10/1985  Stupecky ............................. 128/725

Primary Examiner—Edward M. Coven
Assistant Examiner—John P. Lacyk
Attorney, Agent, or Firm—Emmanuel J. Lobato; Robert E. Burns

[57] ABSTRACT

An inhalation sensor using a thin film pre-stressed diaphragm, senses by optoelectronic means the inhalation and exhalation of air from the nostrils and/or mouth of a patient. The inhalation sensor is used for inhalation therapy by triggering a prescribed dose of therapeutic gas when inhalation takes place. The inhalation sensor can also be used as a monitor to detect apnea (the absence of breathing).

7 Claims, 3 Drawing Sheets

SECTION 1-1

OPTOELECTRONIC INHALATION SENSOR FOR MONITORING INHALATION AND FOR INHALATION THERAPY

BACKGROUND OF THE INVENTION

This invention pertains to using an optoelectronic sensor for inhalation therapy and inhalation monitoring, and particularly using it with such apparatus and operating methods which feature the triggering of a prescribed dose of therapeutic gas when inhalation takes place and/or detects when apnea (the absence of breathing) occurs.

The advantage of using an inhalation sensor as an apnea monitor, is that the inhalation sensor can detect obstructions in the upper air passageways immediately. Other techniques requiring electrodes to be positioned on the chest suffer from a fundamental deficiency in that they measure the thoracic effort rather than specific airway opening and patency.

The inhalation sensor, when used as an apnea monitor, overcomes this problem as it is measuring air flow at an airway opening such as the nasal openings, or if necessary, at the mouth.

A fundamental limitation of detecting inhalation with a sensor is the recognized difficulty of keeping the inhalation sensor aligned with the airway exchange.

The applicant deals with this recognized difficulty by using the nasal cannula (which is an accepted method of administering oxygen for inhalation therapy) as a means of connecting a patient to the inhalation sensor.

This optoelectronic sensor is an improvement over the device shown in the inventor's pending application, "Method and apparatus for using an inhalation sensor for monitoring and for inhalation therapy", received by Commissioner of Patents and Trademarks Feb. 20, 1986.

The optoelectronic sensor, when used with the nasal cannula for inhalation therapy, requires that the negative pressure (which can be as little as 0.001 ounce per square inch) from the nasal openings be transmitted to the sensor through the nasal cannula; that the sensor will detect this low pressure and immediately trigger a prescribed dose of therapeutic gas, using the same nasal cannula as that used for sensing the nasal negative pressure. Therefore, the sensor and cannula must alternately sense 0.001 ounce per square inch negative pressure, and withstand a pressure of 10 pounds per square inch when a dose of therapeutic gas is triggered.

In prior art, the sensing used one tube connected to one of the nasal openings, and a second tube connected to the second nasal opening for the high pressure therapeutic gas.

The optoelectronic sensor in this application requires only a single tube connected to the two prongs inserted in the patient's nasal openings to serve the sensor and supply the therapeutic gas.

The optoelectronic sensor uses an extremely thin diaphragm that is pre-stressed, and to which a very small vane is attached thereto. Very small movements of the vane are sensed by optoelectronic means.

The advantage of using optoelectronics is, if the sensor is manufactured out of opaque material it is not affected by ambient light nor by strong electric fields which create problems when capacitance type of sensors are used.

The greatest difficulty to overcome in sensors using diaphragm movement is maintaining a fixed calibration point. The diaphragm must be responsive to pressures of 0.001 ounce per square inch, yet it must be able to withstand an accidental overload of 10 pounds per square inch without change in the fixed calibration point. The calibration point is affected by the temperature changes that affect the mechanical parts and the characteristics of the electronic circuit.

When the sensor is adjusted for maximum sensitivity, the slightest change in the calibration point will cause undesired oscillation because the high pressure of the triggered dose of therapeutic gas is inadvertently being fed back into the input of the sensor causing parasitic oscillations which could mimic the breathing of the patient.

The applicant's invention deals with this difficulty by making the sensor mechanically stable and providing temperature compensation for the electronic circuit and providing a means of manual adjustment of the calibration point to overcome the parasitic oscillations.

SUMMARY OF THE INVENTION

This invention relates to an inhalation sensor that monitors the inhalation and exhalation of air from the nostrils and/or mouth of a patient, and more particularly, to a sensor that is actuated by a pressure as little as 0.001 ounce per square inch.

A principal object of this invention is to provide an inhalation sensor which can be used for inhalation therapy and apnea monitoring.

Another principal object of this invention is that the inhalation sensor be capable of being manufactured at very low cost by the use of an extremely thin diaphragm, that is pre-stressed, and to which a small vane is attached. Movement of the vane is sensed by optoelectronic means to detect inhalation.

Another principal object of this invention is that the everyday nasal cannula used in hospitals for administering oxygen to a patient is the means of connecting the patient's nasal airflow to the inhalation sensor. If a patient breathes by shifting from nose to mouth, the cannula would be replaced with a mouth/nose mask.

Another principal object of this invention is to use the cannula connected to a patient's nostrils to sense inspiration.

Another principal object of this invention is to supply dose of therapeutic gases or aerosols to a patient via the same cannula.

Another principal object of this invention is that the inhalation sensor be actuated by a pressure as low as 0.001 ounce per square inch and be capable of withstanding a high pressure of 10 pounds per square inch without damage or loss of calibration if the nasal cannula is accidentally stepped on when a triggered dose of therapeutic gas is sent through the cannula.

Another principal object of this invention is that the inhalation sensor has no electrical connection to a patient. It is a passive device that incurs no hazards which can be associated with an electrical circuit.

Another principal object of this invention is that the employment of low current and voltage makes possible an intrisically safe design of this device so it can be used with flammable therapeutic gases.

Another principal object of this invention is that the inhalation sensor can be used for inhalation therapy. The inhalation sensor can supply a dose of therapeutic gas each time a patient inhales. This means that since a patient inhales approximately 30% of the time, a possible saving of 70% of the oxygen used in a continuous flow system can be obtained. It also makes possible a greater volume of oxygen at an early stage of inspiration, and is more effective than conventional continuous flow because oxygen applied during the later stages of inspiration remains in "dead spaces" such as the pharynx, trachea, and bronchial tubes. Oxygen given in the early stage of inspiration is most effective in reaching the alveoli.

Another principal object of this invention is to reduce the potential hazard resulting from oxygen of continuous flow systems not being absorbed by a patient and being present in the environment.

Another principal object of this invention is to make possible such efficient use of oxygen that patients can use small portable oxygen tanks for greater freedom.

Another principal object of this invention is that a filter is inserted in the gas supply being inhaled into a patient's lungs to prevent any foreign object, which may be present, being inhaled.

Another principal object of this invention is that a pre-set time for gas flow can be adjusted to match the breaths per minute for babies and adults.

Another principal object of this invention is when a patient is receiving inhalation therapy, the movement of the float in the tapered tube of a variable area flow meter indicating the number of liters per minute, will indicate if the cannula becomes dislodged or if apnea occurs.

Another principal object of this invention is to provide intermittent gas or aerosol flow to reduce the high cost involved in supplying a patient with continuous flow.

Another principal object of this invention is to detect upper air passageway obstructions. Currently available monitors are dependent on impedance pneumography and heart rate indications. Such devices can not immediately detect obstructions in the upper air passageways. Inhalation sensors detect nasal and/or mouth airflow and, therefore, give immediate detection.

Another principal object of this invention is to detect when a patient stops breathing and approaches death. Monitoring would detect patients who might lapse into a coma due to the hazards of reaction to, or side effects of, drugs. Detection of apnea in infants might prevent deaths due to sudden infant death syndrome.

Another principal object of this invention is to make this optoelectronic inhalation sensor mechanically stable, provide temperature compensation for the electronic circuit, and provide a means of manual adjustment of the calibration point to overcome parasitic oscillations due to undesired oscillations being fed back into the input from the high pressure triggered dose of therapeutic gas.

Another principal object of this invention is that it prevents the back pressure present in continuous flow of oxygen systems when the patient is exhaling carbon dioxide.

Still another object of this invention is to use optoelectronics with opaque materials to prevent interference from ambient light and prevent stray electric fields from affecting the operation that would occur if capacitance type of sensors were used.

DETAILED DESCRIPTION OF THE DRAWINGS

Figure 1:
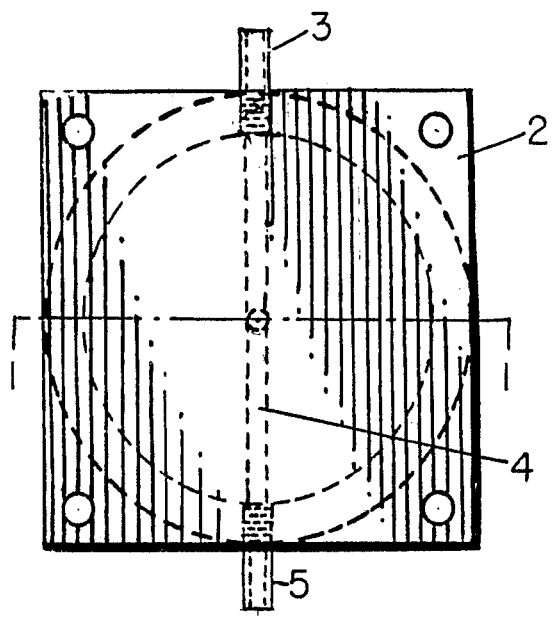

FIG. 1—is a top view of the optoelectronic inhalation sensor according to the invention.

Figure 2:
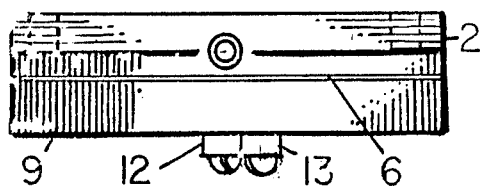

FIG. 2—is a front elevation view of the optoelectronic inhalation sensor according to the invention.

Figure 3:
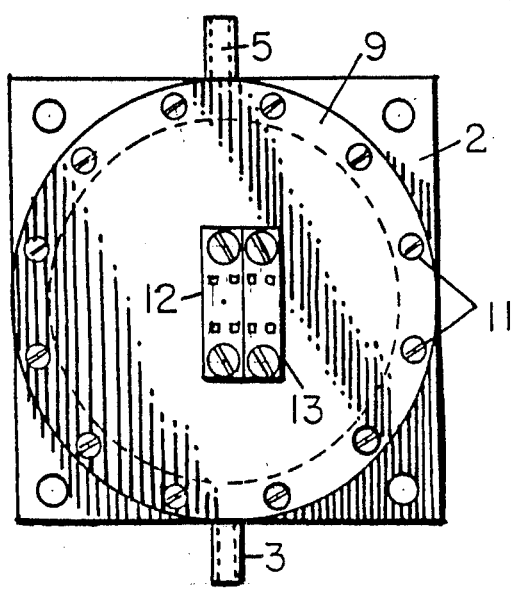

FIG. 3—is a bottom view of the optoelectronic inhalation sensor according to the invention.

Figure 4:
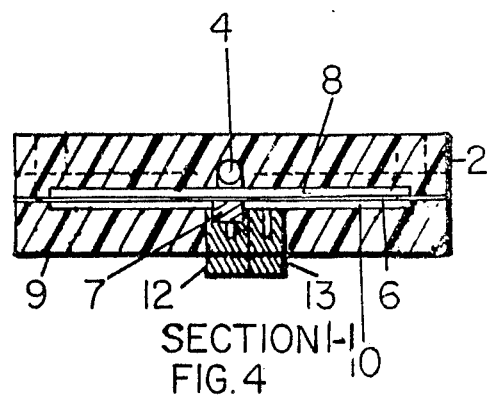

FIG. 4—is a section taken along section line 1—1 of FIG. 1.

Figure 5:
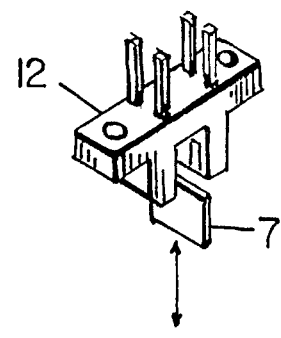

FIG. 5—is a diagrammatic view of an optoelectronic solid state photon coupled interrupter module used in the optoelectronic inhalation sensor in isometric projection.

Figure 6:
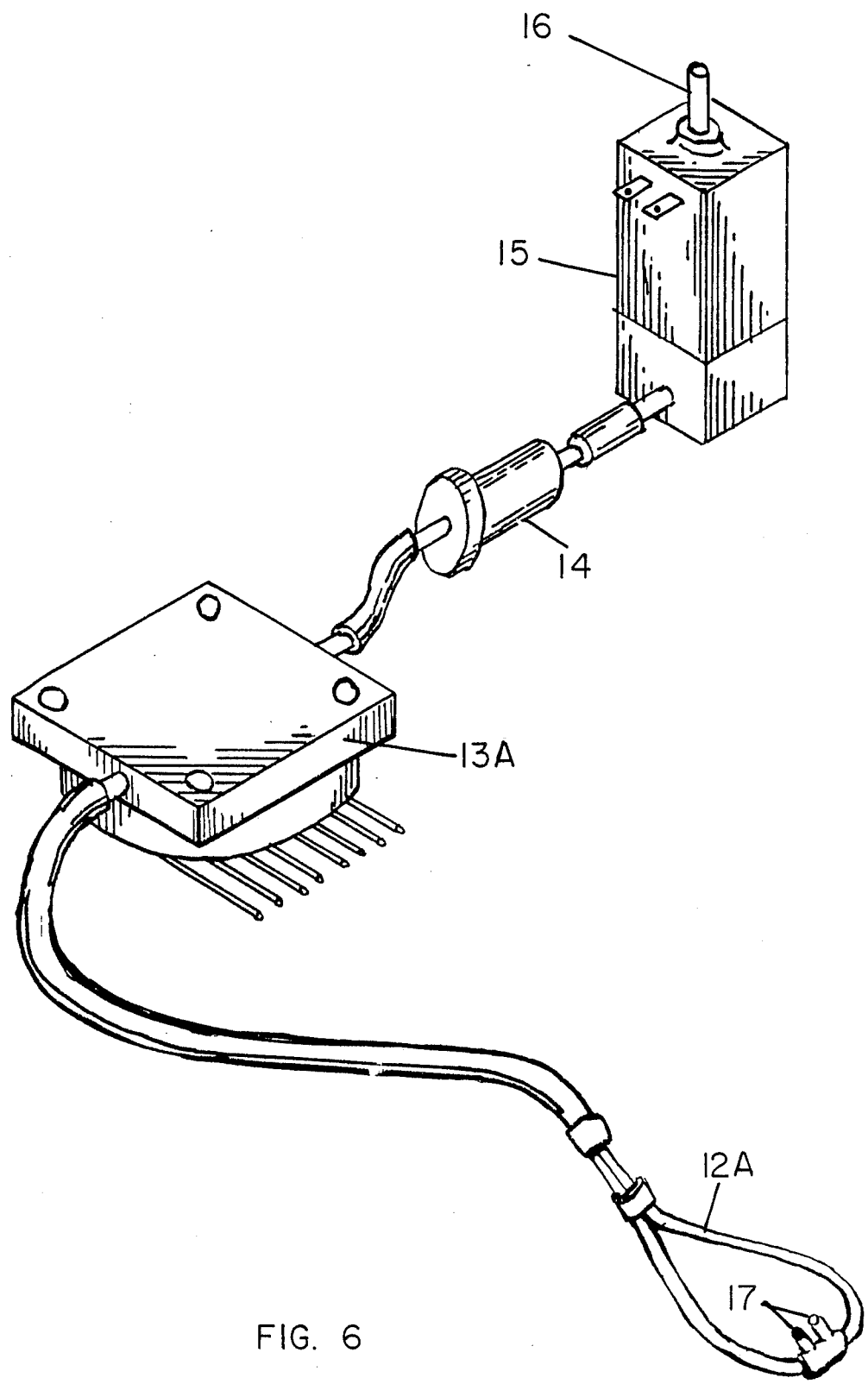

FIG. 6—is a diagrammatic view using an optoelectronic inhalation sensor for inhalation therapy in isometric projection.

Figure 7:
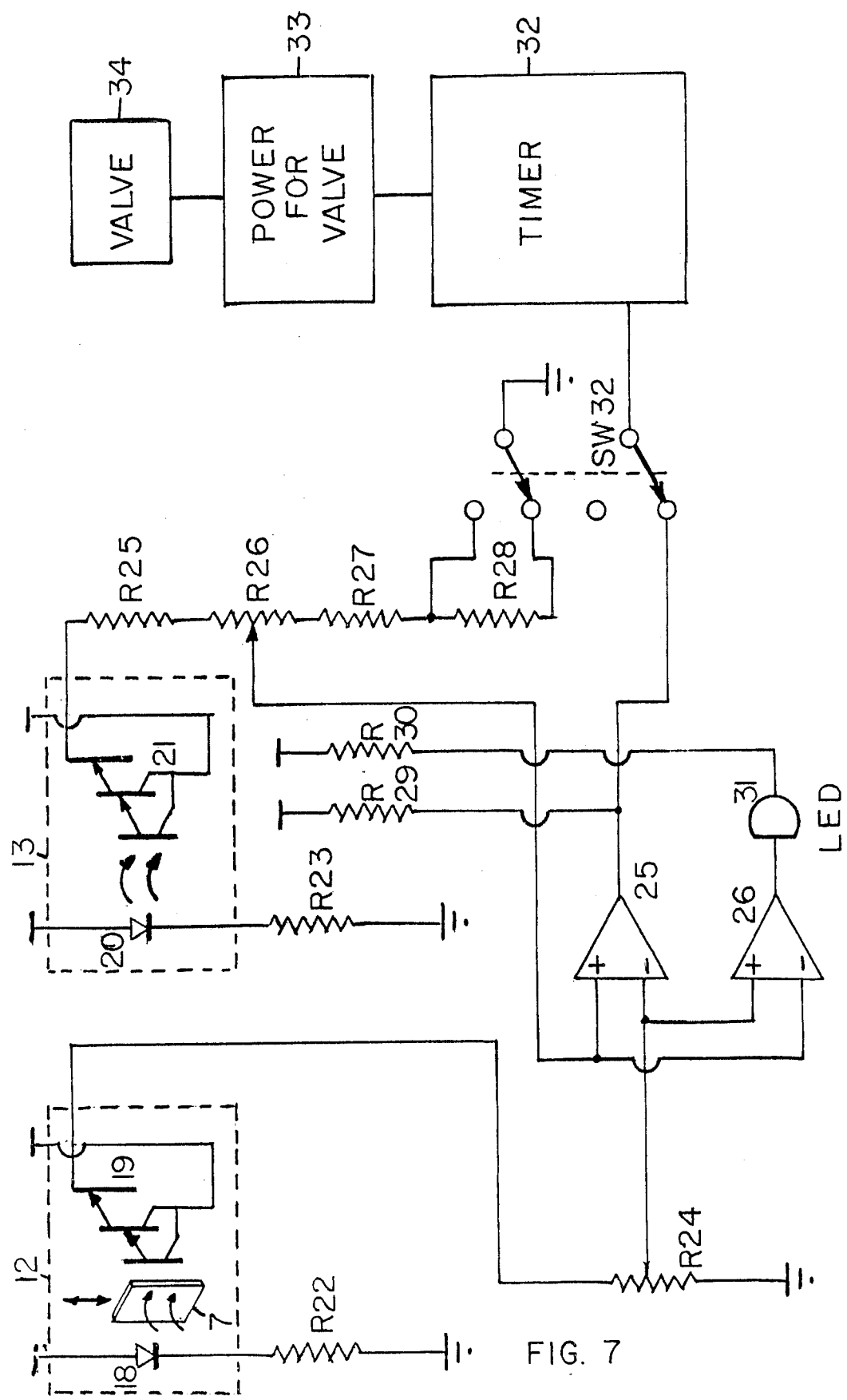

FIG. 7—is a schematic diagram and block diagram for using the inhalation sensor for inhalation therapy.

DESCRIPTION OF THE PREFERRED EMBODIMENT

FIGS. 1, 2, and 3 generally illustrate a preferred embodiment of an optoelectronic inhalation sensor, which comprises a square housing 2, made of a rectangular opaque electrical non-conductor in cross section FIG. 4, having a circular recess forming a central cavity 8 therein, the square housing 2 having an inlet connection 3, through one end thereof, with a passageway 4, and another outlet connection 5, through the other end of the square housing, both inlet and outlet passages being in direct communication with the central cavity 8 in the square housing 2.

With the flow of inhalation therapy gas into the inlet connection 3, passageway 4 with outlet connection 5 creates a suction in central cavity 8. This slight suction is used to clear out any moisture that may have been entrapped in central cavity 8, which, if not removed, could affect operation of the sensor.

The diaphragm 6 is a 0.0005 inch thick polyester film or other equally suitable thin flexible material. The diaphragm 6 is pre-stressed circumferentially and bonded to the surface of the square housing 2 forming a space between the recessed central cavity 8 of housing 2 and the film diaphragm 6. This space changes when a patient inhales, becoming smaller when inhalation takes place.

A clamping disc 9, made of opaque electrical non-conductor material in cross section FIG. 4, having a circular recess forming a central cavity 10, is fastened to the square housing 2 by a plurality of screws 11.

The circular recess forming the lower central cavity 10, is vented to the outside atmospheric pressure. The depth of the circular recess forming the central cavity 10 is minimum, such as 0.005 inch deep, being used to limit the movement of the film diaphragm 6, to prevent the film diaphragm 6 from being stretched when inhalation therapeutic gases with high pressure of 10 pounds per square inch are supplied to the upper central cavity 8. For best operation of the optoelectronic inhalation sensor, the clamping disc 9 should be located at the bottom of the sensor. With changes in temperature, the diaphragm 6 can expand or contract, however, due to the limited depth of the recess, and due to the force of gravity, the diaphragm will always be in close proximity to the set calibration point, which is the point where the film diaphragm 6 is flat with no pressure on either side.

In the center of the clamping disc 9 is a rectangular opening to accept two optoelectronic solid state photon coupled interrupter modules 12 and 13. Module 12 is located in the center of the disc 9, and provides an electrical output when the infrared-opaque vane 7 is moved upward by the film diaphragm 6. The vane 7 is fastened to the center of the film diaphragm 6. Module 13 is located as near as possible to module 12. Module 13 is used as an inactive unit to provide a reference for temperature compensation.

The electrical output of the optoelectronic solid state photon coupled interrupter module 12 occurs when a negative inhalation pressure is applied to the upper central cavity 8 moving the vane 7 upward to allow passage of the infrared light. This puts the module 12 in the same design category as a mechanical precision limit switch, except that the activating vane 7 is blocking light instead of applying force. Thus, mechanical wear and deformation effects are eliminated. If mechanical precision limit switches were used it would be necessary to make them mechanically adjustable so that the actuating point of the switches would occur when the diaphragm was displaced a critical distance. Using the optoelectronic module 12, it is possible to adjust the actuating point electrically since adjusting the sensitivity of the detector is equivalent to moving a mechanical precision limit switch in and out from the diaphragm.

The diaphragm 6 will be activated by a small volume of negative inhalation pressure of 0.001 ounce per square inch, which will move the infrared-opaque vane 7 up to signal switching the output from an "Off" state to an "On" state.

The "On" state will trigger a prescribed dose of therapeutic gas at high pressure forcing the diaphragm 6 into the lower central cavity 10, and preparing it for the next inhalation, when the diaphragm 6 will be sucked up into the upper central cavity 8.

FIG. 6 shows one method and apparatus for using an optoelectronic inhalation sensor for inhalation therapy. A cannula 12, commonly available in hospitals for administering oxygen, is used to connect the flow of air from a patient's nostrils to the optoelectronic inhalation sensor 13A described above, by using the outlet connection 5, FIG. 1.

The filter 14 can be placed as shown on FIG. 6 or inserted between the cannula 12A and optoelectronic inhalation sensor 13A. Its purpose is to prevent any foreign object, that might be present in the gas supply, being inhaled into the patient's lungs.

The optoelectronic inhalation sensor is connected to the normally open solenoid valve 15 by means of appropriate tubing using the inlet connection 3 of the inhalation sensor 13A. The solenoid valve 15 is electrically actuated by low voltage and low current, that can be supplied by an electronic circuit that can be designed to be intrinsically safe (a circuit that is incapable of having a spark or thermal effect that would be capable of causing ignition of flammable or combustible material in the gas being used for inhalation therapy). The connection 16 on the solenoid valve 15 is connected to the supply of gas being used for therapy. In hospitals, a flow meter and pressure regulator are usually available at the patient's bedside and supply a constant flow of gas (such as 0 to 10 liters of oxygen per minute). Present day practice is for hospitals to have oxygen piped permanently into each room used for patient's care.

For home use where oxygen is delivered in tanks, the apparatus supplied with such tanks includes some type of flow meter and a pressure regulator.

The cannula 12A is adjusted to fit the patient so that the two prongs 17 are inserted into the patient's nostrils. The inhalation flow of air from the patient's nostrils produces a very low pressure or vacuum at the end connected to the inhalation sensor 13A.

The vacuum pressure produced by the patient inhaling is no more than a few thousandths of an ounce per square inch. At the time the patient is exhaling, the electric solenoid valve 15 is electrically activated and shuts off the flow of gas from the therapeutic gas being used. When the patient inhales, the thin film diaphragm 6 is sucked up into the upper central cavity 8, moving the infrared-opaque vane 7 upward to cause an electrical signal to an "On" state. With appropriate electrical circuits as described in this patient specification, a signal is sent for a pre-determined time to cause a flow of therapeutic gas by electrically deactuating the normally open valve 15. In actual practice, it has been found that the flow of air being sucked in by the patient is at a maximum for only a very short period of time, and this peak flow of air vacuum from the patient's nostrils is used to trigger the flow of the therapeutic gas for a pre-set time.

The length of the pre-set time can be adjusted for the correct flow of therapeutic gas for the normal adult rate of 14 to 20 breaths per minute, or for 20 to 40 breaths for babies and toddlers. The respiration rate rises as much as four breaths per minute for every degree of patient's temperature over normal.

The pre-determined time therefore, provides for an intermittent flow of therapeutic gas to the patient. The patient normally inhales approximately for 30% of the time for each breath, with 70% of the breath for exhaling. By setting the pre-set timer to 30% of the breath time, a savings of 70% of the therapeutic gas can be achieved over the normal hospital system of having a constant flow. It is also possible to apply the therapeutic gas at a very early stage of inspiration with a large volume of gas which will reach the alveoli and not waste additional gas that remains in the "dead spaces" such as the pharynx, trachea, and bronchial tubes.

At the time the therapeutic gas flows into the inhalation sensor 13A, high pressure is applied to the diaphragm 6, causing it to be in close contact with the circular recessed surface of the central cavity 10, moving the infrared-opaque vane 7 downward to block the infrared light of the interrupter module 12. Therefore, upon completion of the pre-set time, a signal is sent by the inhalation sensor 13A, to an electrical circuit that actuates the solenoid valve 15 to its closed position and shuts off the flow of therapeutic gas to the inhalation sensor 13A, and the cannula 12A.

Upon completion of the patient's exhaling, the cycle of events will be repeated by the patient again inhaling.

FIG. 7 generally illustrates a schematic diagram and block diagram of one of the preferred means of electrical circuits used to obtain intermittent flow of the therapeutic gas. The two optoelectronic solid state photon coupled interrupter modules 12 and 13 of FIG. 7 are the same modules 12 and 13 shown in FIG. 3 located in the inhalation sensor 13A.

The module 12 is an interrupter module consisting of a gallium arsenide infrared emitting diode 18 coupled to a silicon darlington connected phototransistor 19, interrupted by the infrared-opaque vane 7. Vane 7 is actuated by the diaphragm 6 of the inhalation sensor 13A.

The module 13 is an interrupter module consisting of a gallium arsenide infrared emitting diode 20 coupled to a silicon darlington connected phototransistor 21, used as a temperature compensater to balance the temperature changes of module 12.

Resistors R22 and R23 are current limiting resistors used for keeping the power dissipation below maximum ratings of the infrared emitting diodes 18 and 20.

The output of the darlington connected phototransistor 19 is fed into the loading resistor R24, which is a potentiometer allowing for a variable adjustable voltage tap to feed into the inverting input of the voltage comparators 25 and 26.

In like manner, the output of the darlington phototransistor 21 is fed into the loading resistors connected in series R25, R26, R27, and R28. Resistor 26 allows for a variable adjustable voltage tap to feed into the non-inverting input of the voltage comparators 25 and 26.

The output voltage of the comparators 25 and 26 will swing from full on to full off when the voltages applied to the inputs differ by only about 0.001 volt. Thus a very small movement of the vane 7 will produce a very small voltage change that will result in the output of the comparators 25 and 26 swinging from full off to full on with the voltage being applied to the output resistors R29 and R30. The LED 31 will be illuminated each time the patient exhales, and extinguished each time the patient inhales. The switch SW32 is used for calibrating the sensor. The switch, as shown in FIG. 7, is positioned for normal operation after calibration has taken place.

Placing switch SW32 in the calibration position results in resistor 28 not being in the output load of the darlington connected phototransistor 21, and in disconnecting the output of the voltage comparator 25. With the switch in the calibration position, the potentiometer R26 is adjusted (with the cannula 12A disconnected) so that the LED 31 is made to just illuminate. This is the position of the potentiometer R26 where the position of the vane 7 will be most sensitive to the movement of the diaphragm 6 when inhalation occurs.

The potentiometer R24 is adjusted so that the LED 31 will be just illuminated when potentiometer R26 is set at the mid point. When the sensor is adjusted for maximum sensitivity, the slightest change in the calibration point will cause undesired oscillation because the high pressure of the triggered dose of therapeutic gas is inadvertently being fed back into the input of the sensor causing parasitic oscillations which could mimic the breathing of the patient.

The applicant's invention deals with this difficulty by providing mechanical and electrical means to offset and prevent significant changes in the calibration point. The diaphragm 6 is affected by gravity and temperature. An increase in temperature will cause the diaphragm to expand and gravity will act to pull the diaphragm downward. This difficulty is overcome by limiting the distance (to a very small distance, such as 0.005 inch) that the diaphragm can move to the central cavity 10 of the clamping disc 9.

When the high pressure of the triggered dose of therapeutic gas is applied to the diaphragm 6, the diaphragm 6 is prevented from being stretched beyond its limit of elasticity and beyond the point where the material will expand and return to its original shape only after a time delay. A diaphragm that would be allowed to expand to a point where it would be necessary for it to remember its original shape, with a time delay, would cause a shifting of the calibration point and undesirable parasitic oscillations. Temperature changes and aging of the interrupter module 12 could also cause shifting of the calibration point and undesirable parasitic oscillations.

This is overcome in the Dietz invention by using a second interrupter module 13 to obtain the reference voltage for the voltage comparators 25 and 26. The temperature and aging characteristics of the interrupter 12 is compensated for by the identical temperature and aging characteristics of the interrupter 13. Since the calibration point is set at the maximum sensitivity, the slightest change in the balance of the circuit due to shift in the calibration point, would cause the unit to become inoperable. To prevent very small changes of the calibration point from affecting the operation of the sensor, the resistor R28 is added to the output loading resistors R25, R26, and R27 to desensitize the circuit and make it less affected by very slight changes in the calibration point.

When the calibration switch SW32 is positioned as shown in FIG. 7, the output of the voltage comparator 25 is fed into a timing circuit 32. The timing circuit 32 will be triggered by the patient's inhaling and result in an output that is for a pre-set time interval that provides power for valve 33 to actuate the valve 34, giving the patient a dose of oxygen.

The inhalation sensor 13A can be used to monitor breathing by using widely available known electrical circuits.

It is also possible to combine the functions of inhalation therapy and monitoring as shown in the inventor's pending application, "Method and apparatus for using an inhalation sensor for monitoring and for inhalation therapy", received by the Commissioner of Patents and Trademarks Feb. 20, 1986.

The inventor's patent also provides for fail safe operation, a continuous flow of oxygen will be provided in case of failure of the sensor 13A to operate.

While the invention has been particularly shown and described with references to the preferred embodiments thereof, it will be understood by those skilled in the art that various alterations in form and detail may be made therein without departing from the spirit and scope of the invention. Moreover, while the invention has been particularly shown and described for clinical use (as with a patient for example), it should be understood the invention may be used in conjunction with gas supply or apnea detector in a subject in industrial, aeronautical, subterranean or underwater environments.

I claim:

1. An optoelectronic inhalation sensor for detecting inspiration during breathing cycles of air-breathing animals including humans comprising, means connectable operatively to the respiratory system of an animal or human and having a flexible sensing diaphragm at a calibrated position for sensing individual negative pressures developed at each inspiration during each breathing cycle of said animal or human during breathing thereof, optoelectrical means including sensing means for automatically sensing each movement of the diaphragm in response to said negative pressure developed during the breathing cycles of said animal or human, means in said optoelectrical means for developing an electrical signal at each sensed movement of said diaphragm in response to sensing of the individual negative pressure developed at each said inspiration, means for connecting the sensor to a source of a breathable gas, and means to apply said electrical signal to said source of breathable gas for control of supply of said gas to the sensor for inhalation through said means connectable operatively to said air-breathing animal including humans during inhalation periods of said breathing cycles.

2. An optoelectronic inhalation sensor for detecting inspiration during breathing cycles of air-breathing animals including humans comprising, means connectable operatively to the respiratory system of an animal or human and having a flexible sensing diaphragm at a calibrated position for sensing individual negative pressures developed at each inspiration during each breathing cycle of said animal or human during breathing thereof, optoelectrical means including sensing means for automatically sensing each movement of the diaphragm in response to said negative pressures developed during the breathing cycles of said animal or human, means in said optoelectrical means for developing an electrical signal at each sensed movement of said diaphragm in response to sensing of the individual negative pressure developed at each said inspiration, and means for temperature compensation.

3. An optoelectronic inhalation sensor for detecting inspiration during breathing cycles of air-breathing animals including humans comprising, means connectable operatively to the respiratory system of an animal or human and having a flexible sensing diaphragm at a calibrated position for sensing individual negative pressures developed at each inspiration during each breathing cycle of said animal or human during breathing thereof, optoelectrical means including sensing means for automatically sensing each movement of the diaphragm in response to said negative pressures developed during the breathing cycles of said animal or human, means in said optoelectrical means for developing an electrical signal at each sensed movement of said diaphragm in response to sensing of the individual negative pressure developed at each said inspiration, and means for manually calibrating the sensor for operation at said calibrated position corresponding to a condition in which the diaphragm is flat without pressure on either side thereof.

4. An optoelectronic inhalation sensor for detecting inspiration during breathing cycles of air-breathing animals including humans comprising, means connectable operatively to the respiratory system of an animal or human and having a flexible sensing diaphragm at a calibrated position for sensing individual negative pressures developed at each inspiration during each breathing cycle of said animal or human during breathing thereof, optoelectrical means including sensing means for automatically sensing each movement of the diaphragm in response to said negative pressures developed during the breathing cycles of said animal or human, means in said optoelectrical means for developing an electrical signal at each sensed movement of said diaphragm in response to sensing of the individual negative pressure developed at each said inspiration, and means for making the sensing means for sensing movement of the diaphragm most sensitive to said movement when said inspiration occurs.

5. An optoelectronic inhalation sensor for detecting the act of drawing in a breath, comprising:
a flexible thin film diaphragm,
a central circular recessed cavity having said diaphragm pre-stressed circumferentially and bonded to it,
an infrared-opaque vane fastened to the center of said diaphragm,
a solid state photon coupled interrupter module located in center of said central cavity,
a second solid state photon coupled interrupter module located in close proximity to said solid state photon coupled interrupter,
a second central circular recessed cavity fastened by a plurality of screws to said central circular recessed cavity,
means for holding said diaphragm a minimum fixed distance from said central circular recessed cavity,
means for applying a first negative pressure to said second central circular recessed cavity to change distance of said diaphragm from said central circular recessed cavity,
means for obtaining said first negative pressure from flow of air from patient's airway openings,
means for allowing passage of infrared light to indicate movement of said infrared-opaque vane when said diaphragm is moved by said first negative pressure from said flow of air from patient's airway openings.

6. An optoelectronic inhalation sensor as recited in claim 5, further comprising:
means for applying a flow of therapeutic gas to the said second central circular recessed cavity,
means for limiting travel of said diaphragm for preventing rupture from high pressure,
means for removing any moisture in said second central circular recessed cavity.

7. An optoelectronic inhalation sensor as recited in claim 5, further comprising:
means for blocking passage of infrared light to indicate movement of said infrared-opaque vane when said diaphragm is moved by positive exhalation pressure from said flow of air from patient's airway opening.

* * * * *